(12) United States Patent
Albeck et al.

(10) Patent No.: US 7,276,628 B2
(45) Date of Patent: Oct. 2, 2007

(54) BIOLOGICALLY ACTIVE COMPLEX

(75) Inventors: Michael Albeck, Ramat Chen (IL); Benjamin Sredni, Kfar Saba (IL)

(73) Assignee: BioMAS Ltd., Tel-Aviv (IL)

( * ) Notice: Subject to any disclaimer, the term of this patent is extended or adjusted under 35 U.S.C. 154(b) by 373 days.

(21) Appl. No.: 10/496,729

(22) PCT Filed: Nov. 24, 2002

(86) PCT No.: PCT/IL02/00936

§ 371 (c)(1), (2), (4) Date: May 21, 2004

(87) PCT Pub. No.: WO03/044038

PCT Pub. Date: May 30, 2003

(65) Prior Publication Data

US 2005/0004091 A1  Jan. 6, 2005

(30) Foreign Application Priority Data

Nov. 22, 2001 (IL) .................................. 146694

(51) Int. Cl.
C07C 391/00 (2006.01)
(52) U.S. Cl. ..................................... 562/899
(58) Field of Classification Search ............... 562/899; 514/450

See application file for complete search history.

(56) References Cited

U.S. PATENT DOCUMENTS 4,752,614 A * 6/1988 Albeck et al. ............... 514/450
4,761,490 A * 8/1988 Albeck et al. ............... 549/347
4,929,739 A 5/1990 Sredni et al.
5,093,135 A 3/1992 Albeck et al.

FOREIGN PATENT DOCUMENTS

EP 0 194 393 9/1986
EP 333 263 B1 9/1989

OTHER PUBLICATIONS

Albeck, Ammon, et al., "Tellurium Compounds: Selective Inhibition of Cysteine Proteases and Model Reaction with Thiols", Inorganic Chemistry, vol. 37, No. 8, pp. 1704-1712.
Denney, Donald, et al., "Preparation and NMR Studies of Tetraalkoxyselenuranes and Tetraalkoxytelluranes", Journal of the American Cancer Society, 1981, vol. 103, pp. 2340-2347.
Giuseppe, Pietra, et al., "The Effects of Carcinogenic Chemicals in Newborn Mice", Cancer, 1961, vol. 19, pp. 308-317.
Gills, Steven, et al., "T Cell Growth Factor: Parameters of Production and A Quantitative Microassay for Activity", The Journal of Immunology, 1978, vol. 120, pp. 2027-2032.
Uchiyama, Takashi, et al., "A Monoclonal Antibody (anti-Tac) Reactive with Activated and Functionally Mature Human T Cells", The Journal of Immunology, 1981, vol. 126, pp. 1398-1403.
Mbabazi, Jolocam, "Sugar complexes of Sn(IV), Sb(V), and Te (VI) hydroxyanions", Carbohydrate Research, 1985, vol. 140, pp. 151-154.

* cited by examiner

*Primary Examiner*—Johann R Richter
*Assistant Examiner*—Lalitha Nagubandi

(57) ABSTRACT

The invention relates to an aqueous solution containing at least one species selected from the group consisting of a 1:1 molar complex of $TeO_2$ with a moiety of formula (A) and ammonium salts thereof: HO—X—OH (A); where X is an optionally substituted divalent saturated hydrocarbon group containing 2-8 carbon atoms in the chain connecting the two OH groups; and its use for stimulating cells to produce cytokines and for treating mammalian diseases and conditions responsive to increased production of cytokines. The complex may be used also for treating mammalian cancer which is not responsive to increased production of cytokines.

8 Claims, 2 Drawing Sheets

BIOLOGICALLY ACTIVE COMPLEX

This Patent Application claims the benefit of and priority to International Application No. PCT/IL2002/000936, filed on Nov. 24, 2002, which claims the benefit of and priority to Israel Patent No. IL 146694, filed on Nov. 22, 2001, the entire contents of which are hereby incorporated by reference.

BACKGROUND OF THE INVENTION

In U.S. Pat. No. 4,761,490, there are described inter alia certain compounds of tellurium, which are active in vitro and in vivo for the production of cytokines, and are also useful for treating a number of diseases. Other than $TeO_2$ and certain other specific instances, the described active compounds may be regarded as Te tetrahalides in which two Te-halogen bonds have been replaced by two Te—O bonds (where the two oxygen atoms formed originate in an aliphatic diol), with simultaneous displacement of the two hydroxyl hydrogen atoms. In U.S. Pat. No. 4,929,739 and EP 0333263, there are described inter alia, biologically active complexes of $TeO_2$ with mono- or poly-hydroxy polycarboxylic acids, or polycarboxylic acids such as citric acid and tartaric acid. The entire contents of U.S. Pat. Nos. 4,761,490 and 4,929,739, and of EP 0333263, are incorporated herein by reference.

It has surprisingly been found in accordance with the present invention, that biologically useful complexes $TeO_2$ may be formed from ligands other than the mono- or poly-hydroxy polycarboxylic acids, which are the subject of the above-mentioned U.S. Pat. No. 4,929,739 and EP 0333263. Accordingly, it is a primary object of this invention to provide aqueous solutions containing novel water soluble complexes of certain hydroxy-containing compounds.

It is also an object of this invention to provide a pharmaceutical composition which is based on the use of the aforementioned aqueous solutions.

It is a further object of this invention to provide methods for the induction of cytokines using the aforementioned aqueous solutions.

Other objects of the invention will appear from the description which follows.

SUMMARY OF THE INVENTION

The present invention provides in one aspect an aqueous solution containing at least one species selected from the group consisting of a 1:1 molar complex of $TeO_2$ with a moiety of formula HO—X—OH (A) and ammonium salts thereof, where X is an optionally substituted divalent saturated hydrocarbon group containing 2-8 carbon atoms in the chain connecting the two OH groups, the solution containing also, optionally at least one pharmaceutically acceptable water-miscible solvent.

In formula (A), X is substituted by at least one substituent selected from among the following, namely, hydroxy, halogen, cyano, $C_{1-5}$-alkyl, $C_{1-5}$-alkoxy, $C_{1-5}$-haloalkyl, $C_{1-5}$-hydroxyalkyl, $C_{1-5}$-alkanoyloxy, carboxy, $C_{1-5}$-carboxyalkyl, $C_{1-5}$-carbamoylalkyl, $C_{1-5}$-cyanoalkyl, carbamoyl, N-mono-($C_{1-5}$-alkyl)carbamoyl, N,N-di-($C_{1-5}$-alkyl)carbamoyl, ($C_{1-5}$-alkyl)carbonyl, ($C_{1-5}$-alkyl)carbonyl-($C_{1-5}$-alkyl), ($C_{1-5}$-alkoxy)carbonyl, ($C_{1-5}$-alkoxy)carbonyl-($C_{1-5}$-alkyl) and ($C_{1-5}$-alkoxy)-$C_{1-5}$-alkyl.

In a particular embodiment, the moiety of formula (A) is selected from among compounds having formulae (A') and (A"):

$$R^1R^3CH(CH_2)_nCHR^2R^4 \qquad (A')$$

$$R^1R^3CH(CHOH)_nCHR^2R^4 \qquad (A''),$$

where n is 0-6, $R^1$, $R^2$, $R^3$ and $R^4$ are each independently selected from hydrogen and the substituents specified in the preceding paragraph.

Non-limiting embodiments of moiety (A) are ethane-1,2-diol, propane-1,2-diol, butane-1,2-diol, butane-2,3-diol, propane-1,3-diol and butane-1,3-diol.

In another aspect the invention provides a pharmaceutical composition (especially one adapted for oral, parenteral, nasal or topical administration), which comprises the complex of the invention and at least one pharmaceutical carrier, diluent or adjuvant. The invention moreover provides a method for stimulating cells to produce cytokines, either in vivo or in vitro, which comprises contacting cytokine producing cells with an aqueous solution or a pharmaceutical composition according to the invention. The invention still further provides use of the inventive aqueous solution for the manufacture of a medicament for treatment of a mammalian disease or condition responsive to increased production of cytokines and(or) their receptors in the mammalian body and which is selected from cancer, immune deficiencies, autoimmune diseases, neurodegenerative diseases and infectious diseases, wherein the amount of complex of formula (A) present in said medicament is an amount which is effective for such treatment.

The invention yet further provides use of the inventive aqueous solution for the manufacture of a medicament for treatment of a mammalian cancer which is essentially unresponsive to increased production of cytokines and(or) their receptors in the mammalian body, wherein the amount of complex of formula (A) present in said medicament is an amount which is effective for such treatment.

In another aspect, there is provided a process for preparing an aqueous solution according to the invention, wherein (i) a reactant selected from:

a telluric(IV) halide having the formula X(—O—)$_2$Te(hal)$_2$, a telluric(IV) bis-ester having the formula X(—O—)$_2$Te(—O—)$_2$X$^1$, and an ammonium salt having the formula $(NH_4)^+[X(—O—)_2Te(hal)_3]^-$, where X and $X^1$ are each independently selected optionally substituted divalent saturated hydrocarbon groups containing 2-8 carbon atoms in the chain, and hal is a halogen atom, is subjected to hydrolysis in an aqueous medium; or (ii) said aqueous solution obtained in (i) is mixed with an ammonium salt of a salt-forming acid in an aqueous medium, in order to convert the solution of complex (not in ammonium salt form) to the ammonium salt form.

DETAILED DESCRIPTION OF THE INVENTION

The state of prior knowledge regarding the interaction of Te(IV) halides and esters with water may be summed up by the following quotation: "Te(IV) compounds such as $TeX_4$ and $Te(OR)_4$ interact readily with nucleophiles, (and) . . . may . . . eventually hydrolyze to $TeO_2$ in aqueous solution (Albeck, A., et al., Inorganic Chemistry, 37(8):1704-1712 (1998), see page 1705, col.1, lines 17-20).

If, however, in the process of the invention (for example, see above), the starting materials merely hydrolyze to $TeO_2$ and an organic moiety, then it should follow that since the organic moieties are not biologically active in the present context, the biological activity of $TeO_2$ and the formed aqueous solution should be identical under comparable conditions. The fact that this is not the case (see e.g. Examples 13, 14 and 16, infra) support the existence of the present complexes, and contradict the possibility that the aqueous solutions contain merely $TeO_2$ and an organic moiety. The existence of the complexes is further illustrated by the differing solubilities in phosphate buffer solution (PBS) at pH7, of the starting materials for the present process, compared with $TeCl_4$ and $TeO_2$ (stated in mg Te/100 ml PBS, see below for identity of starting materials):

| | |
|---|---|
| preparation 1 | 21 ± 1.0; |
| preparation 3 | 16 ± 0.4; |
| $TeCl_4$ | 2.3 ± 0.1; |
| $TeO_2$ | 2.4 ± 0.1. |

Moreover, the product of preparation 3 cannot be formed by merely mixing the components, $TeO_2$ and ethane-1,2-diol, which must be refluxed together for reaction to take place.

Figure 1:
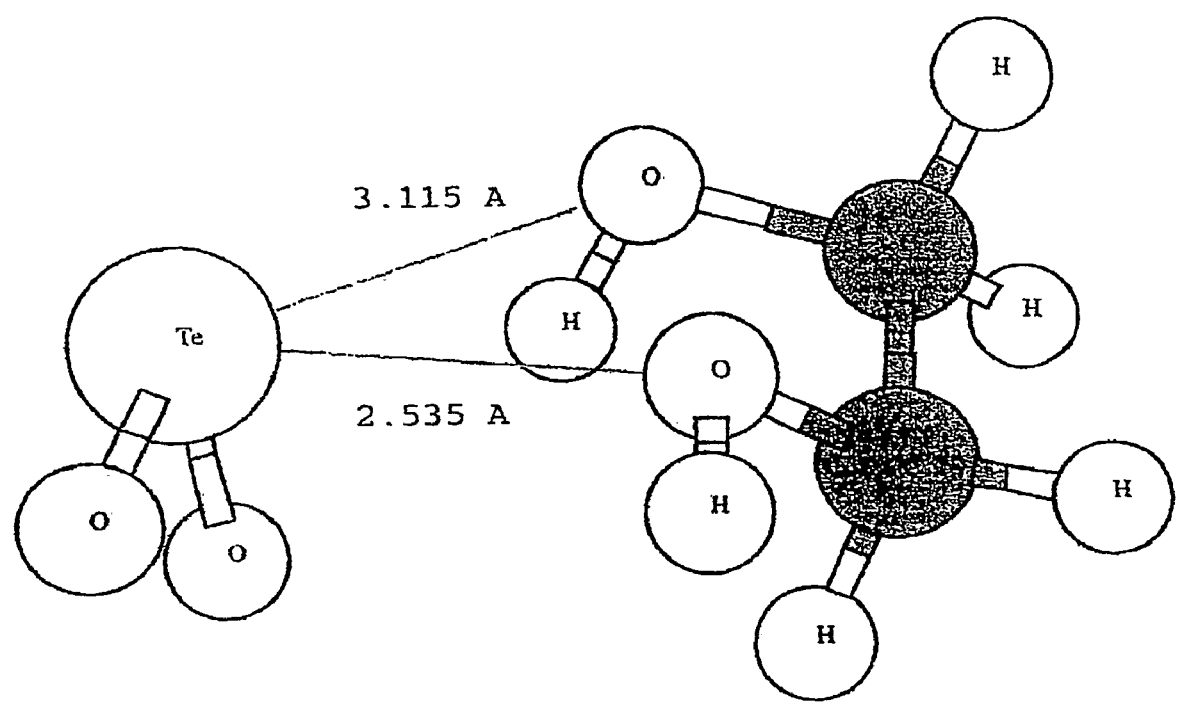
FIG. 1 depicts a possible structure for the 1:1 complex of $TeO_2$ and ethane-1,2-diol, in accordance with a particular embodiment of the invention.
Figure 2:
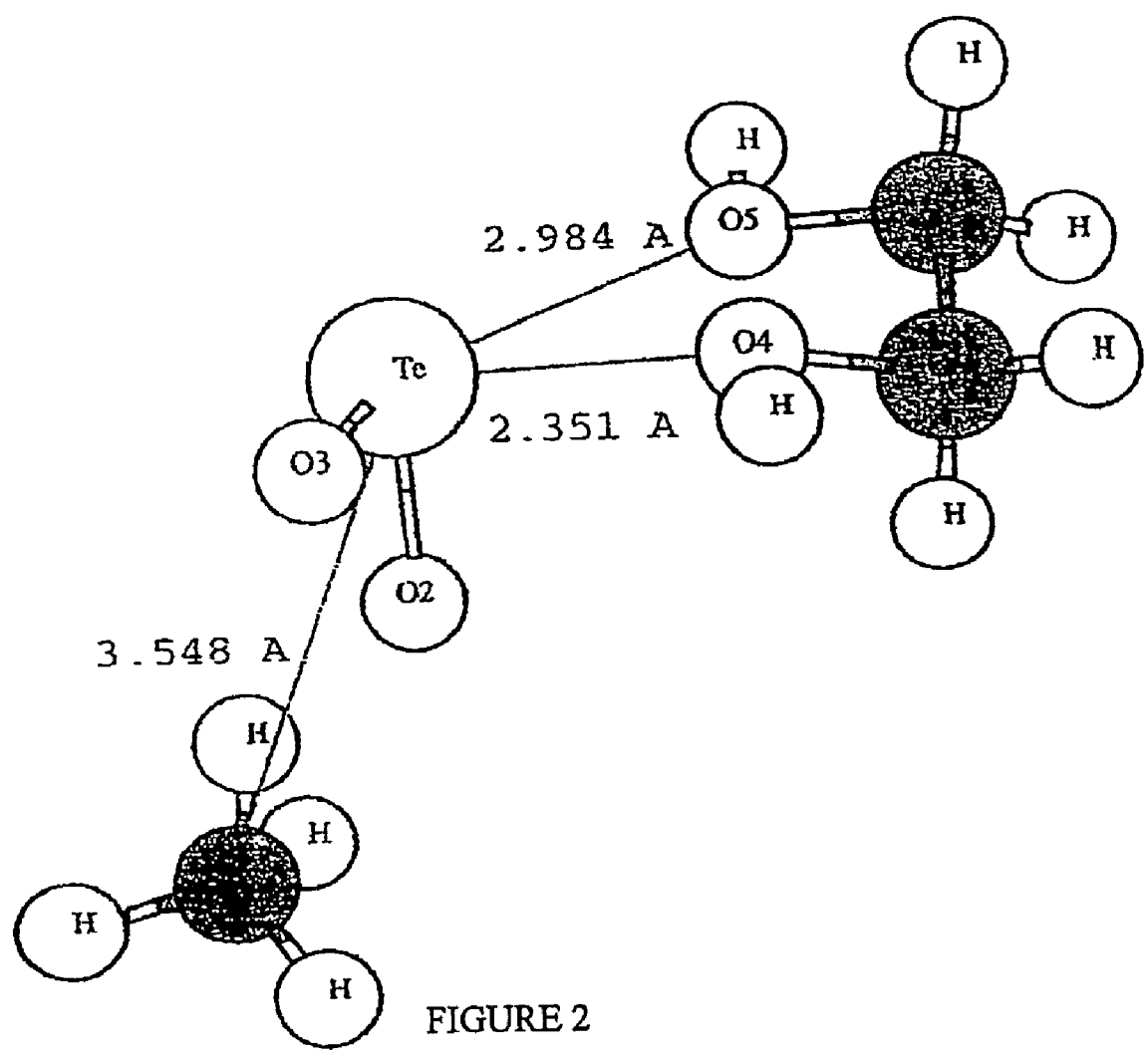
FIG. 2 depicts a possible structure for the ammonium salt of the 1:1 complex of $TeO_2$ and ethane-1,2-diol, in accordance with a particular embodiment of the invention.

While the present invention is not to be regarded as limited by any theory, nevertheless, unpublished studies by the present inventors demonstrate that, e.g., $TeO_2$ and ethane-1,2-diol from the hydrolysis in aqueous solution of the product of Preparation 1, can form a thermodynamically stable complex, which is a well defined species in aqueous solution (see the illustrative model depicted in FIG. 1), and that the ammonium moiety associated with this complex at a N—Te distance of about 3.5 Å (see the illustrative model depicted in FIG. 2), has a stabilizing effect on the non-ammonium form of the complex of about 39 kcal/mole.

The discussion in the preceding paragraph is not to be regarded as excluding the possibility that other entities could be present in the aqueous solution of complex resulting from hydrolysis of the starting materials.

The complexes of the invention may be administered to mammals for treatment of cancer, immune deficiencies, autoimmune diseases neurodegenerative diseases and infectious diseases using amounts that are effective in each condition. The treatment will alleviate the symptoms of these diseases by causing the mammalian body to produce increased amounts of lymphokines. The invention also includes the in vitro production of increased amounts of cytokines such as lymphokines and or their receptors and the use of these materials and/or as therapeutic agents to be administered to mammals for the alleviation of cancer, immune deficiencies neurodegenerative diseases and infectious diseases. It is contemplated that the composition of the Invention may be used in combination with other anti-cancer chemotherapeutic agents such as cyclophosphamide. The term cancer is used to include leukemia and solid tumors that arise spontaneously, by contact with a carcinogenic agent, by irradiation or by oncoviruses. These conditions are well known to those who are skilled in the art and include such conditions as adrenal tumors, bone tumors, gastrointestinal tumors, brain tumors, breast tumors, skin tumors, lung tumors, ovarian tumors, genitourinary tumors and the like. The Merck Manual 13th Edition, Merck & Co. (1977) describes many of these conditions. Pages 647-650; 828-831; 917-920; 966; 970-974; 1273, 1277, 1371-1376; 1436-1441; 1563; 1612-1615 of the publication are incorporated herein by reference. The term immunodeficiency diseases is used to describe a diverse group of conditions such as Acquired Immunedeficiency Syndrome (AIDS) characterized chiefly by an increased susceptibility to various infections with consequent severe acute, recurrent and chronic disease which result from one or more defects in the specific or nonspecific immune systems. Pages 205-220 of the Merck Manual 13th Edition describe many of these conditions and they are incorporated herein by reference.

The term "autoimmune diseases" includes disorders in which the immune system produces autoantibodies to an endogenous antigen, with consequent injury to tissues. Pages 241-243 of the Merck Manual 13th Edition describe these conditions and they are incorporated herein by reference. Neurodegenerative diseases include disorders of movement, see e.g. the Merck Manual $17^{th}$ Edition, Sec. 14, Ch. 179, which is incorporated herein by reference. The term "infectious diseases" includes those pathologic conditions that arise from bacterial, viral or fungus organisms that invade and disrupt the normal function of the mammalian body. Pages 3-149 of the Merck Manual 13th Edition describe these conditions and they are incorporated herein by reference.

The aqueous solutions of the invention may be administered orally, parenterally, topically or by contacting mucous membranes. The complexes may be administered orally in capsules or tablets that may be prepared using conventional excipients, binders, disintegrating agents and the like. The parenteral route is presently preferred and compositions may be prepared by utilizing the complex in a suitable solvent such as an aqueous buffer and dimethyl sulfoxide or glycerol. The parenteral route may be intramuscular, intraverious, intradermal using a sustained release carrier or subcutaneous. The concentration of the complexes in combination with a pharmaceutical carrier is not critical and is a matter of choice. Remington's Practice of Pharmacy, 9th, 10th and 11th Ed. describe various pharmaceutical carriers and is incorporated herein by reference. The dosage of the complexes of the invention, in the form of aqueous solutions, used to stimulate lymphokine production or treat the specific disease condition described herein, may be varied depending on the particular disease and the stage of the disease. Generally an amount of the complex may be administered which will range from $0.05 \times 10^{-3}$ to $1 \times 10^{-3}$ g/Kg of body weight and preferably from $0.1 \times 10^{-3}$ to $0.5 \times 10^{-3}$ g/Kg of body weight. For example a dosage of 1-3 mg per day for a 75 Kg mammal is contemplated as a sufficient amount to induce lymphokines production but the dosage may be adjusted according to the individual response and the particular condition that is being treated.

In addition to treating the mammalian disorders described hereinabove, the complexes may be utilized for veterinary purposes in the treatment of viral and immune diseases that afflict horses, ungulates and fowl. These disorders may be treated using quantities of the complex that may be used in treating the mammalian disorders described hereinabove.

For in vitro use, cells may be stimulated to produce lymphokines by use of $1 \times 10^{-8}$ to $1 \times 10^{-4}$, preferably $1 \times 10^{-7}$ to $1 \times 10^{-5}$ g of complex per $10^6$ cells/ml. Preliminary toxicity studies in mice have established an $LD_{50}$ of 300 μg/25 g of body weight in 6 week old mice for the complex of Example 1. The complexes may be used as anti-bacterial or anti-viral agents in plants or in animals. Virus infections such as West Nile virus infections in mice are susceptible to the complex of the Example 1 at a dose of 10 μg/day/mouse. Plant bacterial infections such as crown gali caused by *Agrobacterium tumefaciens* may be treated or prevented by the application of a 0.1% solution of complexes of the invention.

The invention also contemplates a method for preparing the complexes of the invention in an aqueous vehicle. This method comprises the use of ultrasound or mechanical agitation for an extended period of time which will dissolve the starting material, such as a compound claimed in U.S. Pat. No. 4,761,490. Generally ultrasound is produced by a transformer which transforms 50/60 hertz, line voltage AC into high frequency electrical energy which is coupled to a transducer. By using piezoelectric ceramics, electrical frequency is converted into mechanical vibration. Typical amplitudes of 0.0003 for 40 k Hz equipment and 0.00007 to 0.001 for 20 k Hz equipment are useful. The transducer may be provided with a booster that is connected to a horn that has means for conducting the ultrasound to a container that holds the liquid for dissolving the compounds to be converted to the complexes of the Invention. Useful devices include small scale ultrasonic cleaners such as the Bronson instrument. It has been found that solutions containing about 5 mg/100 ml of the complex of the invention may be prepared by applying ultrasound for a sufficient period of time to provide an aqueous liquid containing the complex. The time required for this is usually 3 hours to 24 hours. High speed mechanical shakers such as a Tutenhauer shaker or waring blenders may be used for this purpose. The use of an electrically operated agitator will cause the compounds to be converted to the complexes to form a solution or dispersion after about 3 to 4 hours of agitation.

It has been discovered that pharmaceutically acceptable water-miscible liquids e.g. glycerol may be used in the preparation of aqueous liquids that contain the complex. These preparations are then diluted with an aqueous injectable diluent such as water, saline solution etc. The preferred diluent is PBS.

It has been found that the complex-containing aqueous solutions in accordance with the present invention can be stored for long periods of time under ambient conditions, e.g. for at least five years.

The following examples are given to illustrate the invention and it is understood that they do not limit the scope of the invention.

Preparation 1 (I: n=0, $R_1=R_2=H$)

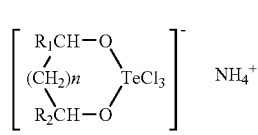

0.01 mol of ethylene glycol and 0.01 mol of tellurium tetrachloride were dissolved in 35 ml of dry acetonitrile and placed in a flask fitted with a reflux condenser and a magnetic stirrer. The reaction mixture was refluxed for six hours. The solution was filtered while hot through a sintered glass filter. The filtrate was collected and allowed to reach room temperature which resulted in the formation of a white precipitate. The precipitate was filtered and collected on a sintered glass filter and washed with cold acetonitrile. It was dried for 10 hours under vacuum of 0.05 mm/Hg. The mp(d) was ca. 200° C.

Preparation 2

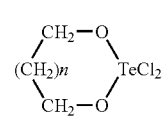

0.01 mol of ethylene glycol was added to 0.01 mol of tellurium tetrachloride in 50 ml of dry benzene in flask fitted with a reflux condenser and a magnetic stirrer. The reaction mixture was refluxed for 16 hours and filtered while hot through a sintered glass filter and worked up as in Example 1 using benzene as a wash liquid to give the compound of formula II where n=0. The mp(d) was ca. 250° C.

Preparation 3 (II: n=0, Y=Z=H)

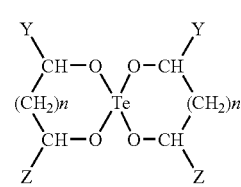

Tellurium dioxide (0.5 mole) was suspended in 250 ml 1,2-ethanediol (excess) and the mixture was heated under reflux at 90° C. under a slight vacuum for 16 hours. A white crystalline product was obtained. The material was separated by filtration, dried and then purified by sublimation at 150° C. (0.25 mm Hg) mp 206.degree.—210° C., Cf. JACS 103, 2340-2347 (1981). Anal. calc. for $C_4H_8O_4Te$: C, 19.2; H, 3.3; O, 25.07; Te 51.2. Found: C, 19.91; H, 3.12; O, 24.98; Te, 49.99. MS m/e 250. This compound has the structure depicted above.

Preparation 4

To a stirred solution of $TeCl_4$ (0.015 mol) and 1,2-propanediol (0.03 mol) in tetrahydrofuran (70 ml) at −40° C. was added dropwise triethylamine (0.06) in 30 ml of tetrahydrofuran. The white precipitate of triethylamine hydrochloride was removed by filtration. The filtrate was concentrated at room temperature and white oily crystals were obtained and purified by sublimation at 120° C. (0.25 mm Hg) M.S. m/e=204,278. This compound has the structure II (n=0, Y=methyl, Z=H).

Preparation 5

Using the procedure of Preparation 1, the following compounds were made using tellurium tetrachloride and the corresponding diol:

| | | |
|---|---|---|
| (a) | I (n = 0, $R_1$ = methyl, $R_2$ = H) | M.S.: 165; 200; 239. |
| (b) | I (n = 0, $R_1$ = $R_2$ = methyl) | M.S.: 165; 200; 253. |

-continued

| | | |
|---|---|---|
| (c) | I (n = 1, $R_1$ = $R_2$ = H) | M.S.: 165; 200; 239. |
| (d) | I (n = 2, $R_1$ = $R_2$ = H) | |

EXAMPLE 1

A solution of the equimolar complex of $TeO_2$ and ethylene glycol, $NH_4Cl$ salt ("complex of Example 1"), was prepared as follows: 5 mg of the product of Preparation 1 was placed in a volumetric flask to which was added 100 ml of a solution of 40% dimethyl sulfoxide (DMSO) and 60% phosphate buffer saline (PBS) solution resulting in a concentration of 10 μg/0.2 ml. If the solution becomes turbid, it is centrifuged at 2000 rpm for ten minutes and the clear supernatant portion is used.

The test animals were Balb-c, male, mice, 6 to 8 weeks of age. All injections were made intraperitoneally using 0.2 ml of the solution of the complex of Example 1 using 25 gauge ⅝" hypodermic needle. The animals received the following injections:
(a) Control (no injection)
(b) Control (0.2 ml DMSO)
(c) 1 μg of the complex of Example 1 in 0.2 ml DMSO/PBS solution
(d) 10 μg of the complex of Example 1 in 0.2 ml DMSO/PBS solution Each of groups a, b, c and d consisted of 21 animals. The animals were sacrificed daily from 24 h to 7 days after injection. On each day, spleen cells from three of the animals from each control group were pooled together and processed by passing the spleen cells through a 60 mesh stainless steel net in a 5 mm Petri dish containing PBS in order to separate the cells. The cells were collected and centrifuged at 1000 rpm for 10 minutes. The supernatant was discarded and the cells were treated for two minutes with 5 ml of hypotonic buffer (0.15M $NH_4$ Cl, 0.01M $KHCO_3$ dissolved in double distilled water, pH 7.2) to kill the erythrocytes. Thereafter, PBS was added to the cells and the cells were centrifuged for 10 minutes at 1000 rpm. The cells were washed twice with PBS and counted in a hemocytometer using trypan blue to test for viability. The cells were brought to a concentration of $10^7$ cells/ml using enriched RPMI containing 10% fetal calf serum (Ser Lab, Sussex, England); $5 \times 10^{-5}$M 2-mercaptoethanol and 3% of d-glutamine (Bio Lab Israel); (stock solution 2 mM×1000 nonessential amino acids) (Bio Lab, Israel); (stock solution×100) and sodium pyruvate (Bio Lab, Israel); (stock solution 1 mM×100). An additional three animals from each of the experimental groups were sacrificed and each of the spleens was processed separately using the same procedure.

The cell mixture was divided into two groups:
(a) Cells at a concentraton of $10^7$ cells/ml enriched RPMI to which was added concanavalin-A (CON A) (DiFCO, Batch 352) 2 μg/ml. These cells were incubated in 5 mm Petri dishes (NUNC) for 24 hours at 37° C., 7.5% $CO_2$. Supernatants were collected, centrifuged at 1,600 rpm for 10 minutes and stored at 4° C. until used. These supernatants were assayed for interleukin-2 (IL-2) and colony stimulating factor (CSF) activity.
(b) Cells at a concentration of $10^7$ cells/ml enriched RPMI which was incubated at 37° C., 7.5% $CO_2$ for 96 h., without addition of CON A. Supernatants were collected, centrifuged and stored at 4° C. until used. These supernatants were assayed for CSF activity. Prior to incubation of the cells, samples were removed from culture plates and smears of the cultures were made by cytocentrifugation. Slides were stained with May-Grunwald-Giemsa (1:10) solution and evaluated morphologically. A radioactive thymidine assay was used to determine IL-2 activity.

Assay for IL-2 Activity

1. Supernatants were tested for IL-2 activity by the proliferation of the IL-2 dependent cell line CTLD. The IL-2 assay is based on the growth dependence of these cultured T-cell lines on IL-2. T cells harvested from IL-2 dependent culture, washed and placed back in culture in the absence of IL-2 invariably die within 24 hr. By using tritiated thymidine incorporation ($^3$H-TdR) as an index of cultured T-cell replication, the IL-2 microassay provides a highly reproducible and quantitative indication of the amount of IL-2 activity in the supernatant prepared hereinabove.

2. To assay a condition medium for IL-2 activity, a sample containing $5 \times 10^4$ CTLD cells, 10% fetal calf serum and 50% of supernatant in question, all were suspended in a final volume of 1 ml RPMI. Aliquots of 0.2 ml from each sample were placed in four replicate wells of 96 microwell tissue culture plates (NUNC). Conditioned medium was obtained from cultures of Charles River rat spleen cells stimulated with Con A that contained a known amount of IL-2 as a reference in all assays.

3. The microwells were incubated for 24 hr. at 37° C. after which 1 microcurie/well of $^3$H-methylthymidine was added. Cells were then further incubated overnight, harvested with a cell harvester, and counted in a beta scintillator. The results, in counts per minute (CPM) were as follows and indicate the relative quantity of IL-2 that is present in the supernatants.
(a) Control (no injection)
(b) Control (0.2 ml DMSO)
(c) 1 μg of complex of Example 1 (in 0.2 ml DMSO/PBS solution)
(d) 10 μg of complex of Example 1 (in 0.2 ml of DMSO/PBS solution)

| | day 1 | day 2 | day 3 | day 4 | day 6 | day 7 |
|---|---|---|---|---|---|---|
| (a)* | 37.695 | 32.055 | 24.758 | 45.029 | 25.065 | 36.775 |
| (b)* | 16.323 | 30.824 | 24.861 | 30.555 | 48.921 | 38.626 |
| (c) | 25.919 | 21.398 | 10.130 | 31.999 | 41.261 | 66.854 |
| (c) | 34.326 | 22.050 | 13.235 | 14.226 | 80.314 | 58.094 |
| (c) | 16.718 | 9.338 | 2.176 | 17.228 | 42.485 | 51.268 |
| (d) | 24.335 | 31.901 | 20.316 | 26.644 | 22.040 | 85.216 |
| (d) | 21.193 | 36.390 | 18.288 | 18.051 | 74.043 | 6.299 |
| (d) | 25.381 | 22.066 | 12.126 | 65.963 | 43.838 | — |

*spleens from control animals were pooled after removal from animal.

EXAMPLE 2

This example describes the stimulation of IL-2 production from human mononuclear cells by the use of the complex of Example 1. Venous whole blood (with heparin, Evans: 10 IU/ml blood) was diluted with RPMI in a ratio of 1:1. The diluted blood was gently placed on Lymphoprep (Nylgard & Co., Oslo, Norway, density 1.077 g/ml) two parts of diluted blood on one part of Lymphoprep. Each tube was provided with 3 ml Lymphoprep and 6 to 7 ml diluted blood. The tubes were centrifuged 30 minutes at 1600 rpm at room temperature. After the centrifugation, mononuclear cells were collected from the interphase fraction and washed with RPMI three times. The cells were resuspended in RPMI, counted on a hemocytometer, using trypan blue to test for viability and brought to a concentration of $1\times10^6$ cells per ml in enriched RPMI. Varying concentrations of the complex of Example 1 ranging from 50 pg/ml to 5 pg/ml were added in a volume of 10% of cell mixture. Aliquots of 0.2 ml from each sample were placed in wells of microplates (NUNC) (triplicates). The microplates were incubated for 72 hours at 37° C. after which 3H-methylthymidine, 1 μCi/well (Nuclear Research Center, Israel) was added to the cultures. Cells were further incubated overnight and harvested with a cell harvester. Proliferation of human mononuclear cells was increased by 5 to 6 fold in the range of 1 to 10 ng/ml of cells of the complex of Example 1 thus suggesting that the complex of Example 1 either induced the production of IL-2 in a subset of the mononuclear cells resulting in the observed proliferation and/or the induced receptor formation in a given population which would also result in proliferation.

EXAMPLE 3

This example illustrates the in vivo effect of the complex of Example 1 on an experimentally induced tumor. A solution of 0.2% of methylcholanthrene (MCA, Sigma, USA) was prepared by dissolving 2 mg of the carcinogen in 1.0 ml of olive oil (Ref: Petra, et al., Cancer 19: 302, 1961) with continuous shaking at 37° C. for 30 minutes. Six to eight week old $C_3$Heb mice were injected with 0.6 mg MCA/0.3 ml of solvent/mouse subcutaneously in the rear right thigh. After 21-30 days the induced tumor was surgically removed and pushed through 60 mesh stainless nets to obtain isolated cells. These cells were then further injected subcutaneously into the rear right thigh of $C_3$Heb mice 5 to 8 weeks of age, at a concentration of $10^6$ cells/0.3 ml PBS/mouse/hypodermic needle 25 gauge, ⅝" to further induce tumor formation. Five days after injection of the tumor cells, a palpable tumor was induced. The animals were thereafter treated as follows:
(a) control (0.2 ml 40% DMSO 60% PBS, IP 1 day after the induced tumor was palpable).
(b) 10 μg of complex of Example 1, IP to 5 mice (in 0.2 ml 40% DMSO 60% PBS, 3 days after the induced tumor was palpable and a second injection of 10 μg of complex in the same solvent was administered 5 days after the first injection to 3 of the 5 mice.

The tumors were excised after 13 days and the volume was determined and is reported in the Table. All animals expired 35 to 38 days after the initial inoculation.

TABLE

| Group | Mouse | Complex of Ex. 1 Administration | Vol. of Tumor (13 days) |
|---|---|---|---|
| a* | 1 | — | 4.01 |
| a* | 2 | — | 3.7 |
| a* | 3 | — | 3.9 |
| b | 7 | day 3 | 0.77 |
| b | 8 | day 3 | 1.66 |
| b | 4 | day 3 and 5 | 0.7 |
| b | 5 | day 3 and 5 | 0.52 |
| b | 6 | day 3 and 5 | 0.31 |

*Control

EXAMPLE 4

Balb-c mice, age 7 weeks were Injected with methylcholanthrene to induce the formation of fibrosarcoma cells according to the procedure of Example 3. The test animals were divided into two groups. (a) control (0.2 IP of 40% DMSO and 60% PBS); (b) 10 pg of the complex of Example 1 (in 0.2 ml 40% DMSO 60% PBS, IP at intervals shown in Table 2).

TABLE 2

| Days After Inoculation With Tumor Cells | Days after Injection With Complex Of Example 1 | % Survival |
|---|---|---|
| (a)* | | |
| 24 | — | 100% |
| 25 | — | 63% |
| 34 | — | 55% |
| 46 | — | 45% |
| 60 | — | 35% |
| 67 | — | 18% |
| 69 | — | 0% |
| (b) | | |
| 4 | 4 | 100% |
| 9 | 9 | 100% |
| 23 | 23 | 100% |
| 30 | 30 | 100% |
| 37 | 37 | 100% |
| 39[1] | 39 | 100% |
| 41 | 41 | 100% |
| 43 | 43 | 100% |
| 46 | 46 | 80% |
| 48 | 48 | 80% |
| 50 | 50 | 80% |
| 53 | 53 | 60% |
| 60 | 60 | 40% |
| 67 | — | 20% |
| 68 | — | 0% |

*Control
[1]Day 39 marked the start of an increased dosage regimen to determine the toxicity of the complex of Example 1. The mortality results for group (b) were 0% until just after the increased dosage regimen.

EXAMPLE 5

This example describes the in vitro production of IL-2 and CSF from mouse spleen cells using the complex of Example 1 as the extrinsic stimulating agent. Spleens were removed from 15, male Balb-c mice 6 to 8 weeks of age. The spleen cells were pushed through stainless steel 60 mesh (U.S. Standard) nets resting in 5 mm Petri dishes containing PBS in order to separate the cells. The cells were then collected into centrifuge tubes and spun at 1000 rpm for 10 minutes. The supernatant was discarded and cells were treated with 5 ml of hypotonic buffer (0.15M $NH_4Cl$; 0.01M $KHCO_3$ dissolved in double distilled water, pH 7.2) for exactly two minutes. Thereafter, PBS was added to the cells and the test tubes were centrifuged for 10 minutes at 1000 rpm. The cells were rinsed twice and counted in a hemocytometer using trypan blue to test for viability. The cells were brought to a concentration of $10^7$ viable cells/ml. The cells were contacted with varying amounts of the complex of Example 1 in 1 ml of 40% DMSO 60% PBS. Table 3 shows the induction of IL-2 activity and colony stimulating factor that was obtained with varying amounts of the complex of Example 1.

TABLE 3

| Complex of Example 1* | IL-2 (cpm) | CSF (colonies/dish) |
|---|---|---|
| 50 μg | 5,000 | 2 |
| 5 μg | 5,000 | 5 |

TABLE 3-continued

| Complex of Example 1* | IL-2 (cpm) | CSF (colonies/dish) |
|---|---|---|
| 500 ng | 5,000 | 25 |
| 50 ng | 6,000 | 75 |
| 5 ng | 15,000 | 120 |
| 500 pg | 30,000 | 175 |
| 50 pg | 38,000 | 260 |
| 5 pg | 12,000 | 140 |

*In terms of amount of starting material produced in Preparation 1.

Control animals injected with the DMSO solvent were found to have a IL-2 baseline of 4,000-5,000 CPM and a CSF of 70-80/colonies/dish.

EXAMPLE 6

Human mononuclear cells were obtained as described above and cultured for 72 hours at a concentration of $10^6$ cells/ml enriched RPMI, in the presence of varying concentrations of the complex of Example 1. Culture supernatants were collected, centrifuged and tested for IL-2 activity by using 50% of the volume of the supernatant assaying their ability to support the proliferation of the IL-2 dependent cell line CTLD. Table 4 reports the results of this assay.

TABLE 4

| Complex of Example 1* | Counts per minute |
|---|---|
| 1 µg | 250 |
| 100 µg | 280 |
| 10 ng | 1,500 |
| 1 ng | 11,000 |
| Control: | |
| CTLD cells | 3,500 |

*In terms of amount of starting material produced in Preparation 1.

EXAMPLE 7

(a) A solution of the equimolar complex of $TeO_2$ and ethylene glycol (Complex of Example 7(a)) was prepared as follows: 5 mg of the product of Preparation 2 was placed in a volumetric flask to which was added 100 ml of a solution of 40% dimethyl sulfoxide (DMSO) and 60% phosphate buffer saline (PBS) solution resulting in a concentration of 10 µg/0.2 ml. If the solution becomes turbid, it is centrifuged at 2000 rpm for ten minutes and the clear supernatant portion is used. The stimulation of IL-2 production from human mononuclear cells by the use of the complex thus produced will now be described. Venous whole blood (with heparin, Evans: 10 IU/ml blood) was diluted with RPMI in a ratio of 1:1. The diluted blood was gently placed on Lymphoprep (Nylgard & Co., Oslo, Norway, density 1.077 g/ml) two parts of diluted blood on one part of Lymphoprep. Each tube was provided with 3 ml Lymphoprep and 6 to 7 ml diluted blood. The tubes were centrifuged 30 minutes at 1600 rpm at room temperature. After the centrifugation, mononuclear cells were collected from the interphase fraction and washed with RPMI three times. The cells were resuspended in RPMI, counted on a hemocytometer, using trypan blue to test for viability and brought to an enriched RPMI. Varying concentrations of the complex ranging from 50 µg/ml to 1 ng/ml were added in a volume of 10% of cell mixture. Aliquots of 0.2 ml from each sample were placed in triplicate wells of microplates (NUNC). The microplates were incubated for 72 hours at 37° C. afterwards with $^3$H-methylthyrmidine, and 1 µCi/well (Nuclear Research Center, Israel) was added to the cultures. Cells were further incubated overnight and harvested with a cell harvester. Proliferation of human mononuclear cells was increased by 10 fold in the range of 1 to 10 ng of the complex of this Example/ml cells thus suggesting that the complex either induced the production of IL-2 in a subset of the mononuclear cells resulting in the observed proliferation and/or the induced receptor formation in a given population which would also result in proliferation.

(b) By proceeding similarly to the first paragraph of Example 7(a), an aqueous solution of the equimolar complex of $TeO_2$ and ethane-1,2-diol was prepared from the product of Preparation 3. Whereas in Example 7(a) the HCl liberated by hydrolysis may be expected to aid complex formation and/or stabilization, this is not the case where the starting material is that of Preparation 3 (cf also the differing biological results shown in the second Table in Example 13, below).

(c) By proceeding similarly to the first paragraph of Example 7(a), an aqueous solution of the equimolar complex of $TeO_2$ and propane-1,2-diol was prepared from the product of Preparation 4.

EXAMPLE 8

To a 100 ml solution of PBS (see Table) is added 5.0 mg of the compound of Preparation 1 using sterile conditions. The mixture is placed in a sonicator, and is sonicated for 4 hours. After the 4 hour period, the compound is dissolved to give a concentration of 10 µg/0.2 ml of the complex of Example 1.

| | |
|---|---|
| NaCl | 8.0 g |
| KCl | 200 mg |
| $Na_2HPO_4$ | 1150 mg |
| $KH_2PO_4$ | 200 mg |
| $CaCl_2$ (anhyd.) | 100 mg/L |
| $MgCl_2$ $6H_2O$ | 100 mg/L |
| $H_2O$ | sufficient to make 1 liter |

EXAMPLE 9

Using 100 ml of the PBS of Example 8, 5.0 mg of the compound of Preparation 1 is dissolved by shaking in an electrically operated shaker for 4 hours, using sterile conditions to obtain a 10 µg/0.2 ml solution of the complex of Example 1.

EXAMPLE 10

Using stirring, 5.0 mg of the compound of Preparation 1 is dissolved under sterile conditions in 20 ml of glycerol. Thereafter 80 ml of PBS is added to form a solution containing 10 µg/0.2 ml of the complex of Example 1. Moreover, it has been determined that the compound of Preparation 1 will dissolve in glycerol/PBS as follows: 6.0 g/l in 40% glycerol/60% PBS; 1.3 g/l in 20% glycerol/80% PBS; 1.0 g/l in 10% glycerol/90% PBS.

EXAMPLE 11

This example demonstrates the effect of oral administration of the complexes of Example 1 and 7(a) on the induction of lymphokines. Aqueous solutions were prepared by dissolving the compounds of Preparations 1 and 2 in PBS at a concentration of 50 µg/ml PBS and diluting the resulting solution to the desired concentration (10 µg/ml of water and 1 µg/ml of water for the compound of Preparation 1 and 25 µg, 10 µg and 1 µg/ml of water for the compound of Preparation 2). The complexes were administered in these dilutions, as drinking water, to male Balb-C mice, 6-8 weeks of age over a 4 day period. The exact amount of liquid intake was recorded daily. After 4 days the mice were sacrificed and spleens removed and processed as described in Example 1. The cells were incubated at a concentration of $10^7$ cells/ml in enriched RPMI containing 2 µg/ml of con-A for 24 hours at 37° C. The supernatants were collected and tested for IL-2 content.

| Complex | µg/ml $H_2O$ | Intake/animal | cpm |
|---|---|---|---|
| Ex 1 | 10 µg/ml | 248 µg | 49179 [+50%]* |
| Ex 1 | 1 µg/ml | 23 µg | 44500 [+35%]* |
| Ex 7(a) | 25 µg/ml | 406 µg | 36815 |
| Ex 7(a) | 10 µg/ml | 123 µg | 42500 [+30%]* |
| Ex 7(a) | 1 µg/ml | 17 µg | 32843 |
| Control | | | |

*Percent increase as compared to control

This experiment shows that the complexes of Examples 1 and 7(a) are active for inducing lymphokine production when given orally in an aqueous diluent.

EXAMPLE 12

By proceeding In the manner described in Example 1, above, there were prepared aqueous solutions of the ammonium salts of the equimolar complexes of $TeO_2$ and (a) propane-1,2-diol, (b) butane-2,3-diol, (c) propane-1,3-diol and (d) butane-1,4-diol, starting with the products of Preparation (a), (b), (c) and (d), respectively.

EXAMPLE 13

This Example shows the stimulative effect of the complexes of Examples 1, 7(a), 7(b), 12(a), compared with $TeO_2$ alone, on the induction of IL-2 receptors of human mononuclear cells. Human MNC were brought to a concentration of $10^6$ cells/ml. RPMI+10% FCS. Aliquots of 0.2 ml. were placed in duplicate wells of microdishes and plates were incubated at 37° C. for 24 hrs. Thereafter wells were rinsed twice with RPMI and cells were resuspended with 20 I.U./ml recombinant IL-2 in RPMI and 10% FCS. Plates were further incubated for 48 hrs. and labeled with $^3H$ thymidine 24 hrs. before harvesting. The proliferation was measured by $^3HT$ uptake as described by Gillis et al, J. Immunol. 120, 2027 (1978). The results are expressed in counts per minute.

| Test A (µg/ml) | Complex of Ex. 1 | Complex of Ex. 1 | Complex of Ex. 12(a)$^x$ | $TeO_2$ | Complex of Ex. 12(a)$^y$ |
|---|---|---|---|---|---|
| 1 | 28625 | 27593 | 21910 | 1563 | 1018 |
| $5 \times 10^{-1}$ | 120755 | 105943 | 145208 | 4667 | 1195 |
| $7 \times 10^{-1}$ | 164538 | 115195 | 130845 | 2475 | 2102 |
| $5 \times 10^{-2}$ | 20022 | 5702 | 8752 | 2515 | 1602 |
| $1 \times 10^{-2}$ | 1952 | 3963 | 9543 | 3108 | 5883 |
| $1 \times 10^{-3}$ | 3652 | 5055 | 6685 | 2867 | 1093 |
| $1 \times 10^{-4}$ | 3558 | 4047 | 6447 | 5540 | 1138 |
| $1 \times 10^{-5}$ | 2474 | 4063 | 8177 | 3442 | 2146 |

$^x$Control −2338 (no chemical)
$^y$Cell plus recombinant IL2 (human) Biogen $1.5 \times 10^{-6}$ units −3260
Note: Phytohemagglutinin M (Difco) 195,432

| Test B (µg/ml) | Complex of Ex. 1 | Complex of Ex. 7(a) | $TeO_2$ | Complex of Ex. 7(b) |
|---|---|---|---|---|
| 1 | 23488 | 9315 | 3275 | 2620 |
| $5 \times 10^{-1}$ | 66910 | 8688 | 5405 | 2402 |
| $7 \times 10^{-1}$ | 17620 | 5250 | 4302 | 2000 |
| $5 \times 10^{-2}$ | 5390 | 5538 | 4280 | 3290 |
| $1 \times 10^{-2}$ | 6057 | 6418 | 3077 | 3928 |
| $1 \times 10^{-3}$ | 5865 | 5167 | 3800 | 3007 |
| $1 \times 10^{-4}$ | 4960 | 5372 | 2925 | 2327 |
| $1 \times 10^{-5}$ | 7155 | 6397 | 3645 | 2242 |

Notes: Control 5573 (no chemical).
Cell plus recombinant IL2 (human) Biogen $1.5 \times 10^{-6}$ units 6858. Phytohemagglutinin M (Difco) 125,272

EXAMPLE 14

This example shows the stimulative effect of the complexes of the invention on the proliferation of human mononuclear cells. Human mononuclear cells were obtained by layering heparinized blood over a Ficoll/Hypaque gradient. The mononuclear cells were resuspended in enriched RPMI, rinsed three times and brought to a concentrations of $5 \times 10^5$ cells/ml enriched RPMI. Varying concentrations of the complexes of Ex. 1 and Ex. 7(a), ranging from 0.005 µg to 5 µg/cell mixture were added to the cells. Aliquots of 0.2 ml of each sample were placed in wells of microplates (triplicates). Microplates were incubated for 72 hours at 37° C. after which they were labelled with $^3H$ methyl-thymidine 1 µCi/well for an additional 24 hours. Cells were then harvested with a cell harvester.

| (µg/ml) | Complex of Ex. 1 | Complex of Ex. 1 |
|---|---|---|
| 1 | 873 | 4700 |
| $5 \times 10^{-1}$ | 18515* | 33700* |
| $1 \times 10^{-1}$ | 2735 | 708 |
| $5 \times 10^{-2}$ | 3865 | 910 |
| $1 \times 10^{-2}$ | 3235 | 1362 |
| $1 \times 10^{-3}$ | 2553 | 2180 |
| $1 \times 10^{-4}$ | 3838 | 2387 |
| $1 \times 10^{-5}$ | 3218 | 2442 |
| control | 2700 | 2943 |

| (µg/ml) | Complex of Ex. 1 | Complex of Ex. 1 | Complex of Ex. 12(a) | $TeO_2$ |
|---|---|---|---|---|
| 5 µg/ml | 5008 | 5182 | 4118 | 3028 |
| 1 µg/ml | 6000 | 5600 | 4557 | 2842 |
| $5 \times 10^{-1}$ | 20488* | 13600* | 18415* | 4773 |
| $1 \times 10^{-1}$ | 7037 | 10382* | 12435* | 4825 |
| $5 \times 10^{-2}$ | 5520 | 5765 | 5953 | 5802 |
| $1 \times 10^{-2}$ | 6898 | 5712 | 6000 | 4730 |
| $1 \times 10^{-3}$ | 5800 | 6000 | 6300 | 6168 |
| $1 \times 10^{-4}$ | 5513 | 6212 | 4587 | 5331 |
| Control | 3600 | 6117 | 6113 | 4912 |

-continued

| μg/ml | Complex of Ex. 7(a) | Complex of Ex. 7(a) |
|---|---|---|
| 1 | 4557 | 943 |
| $5 \times 10^{-1}$ | 18415 | 23957* |
| $1 \times 10^{-1}$ | 12435 | 31424* |
| $5 \times 10^{-2}$ | 5953 | 5532 |
| $1 \times 10^{-2}$ | 6000 | 2987 |
| $1 \times 10^{-3}$ | 6300 | 1510 |
| $1 \times 10^{-4}$ | 4321 | 2332 |
| $1 \times 10^{-5}$ | 5118 | 2481 |
| Control | 4587 | 2018 |

*The concentrations that induced proliferation range from $5 \times 10^{-1}$ to $1 \times 10^{-1}$ μg. No significant effect was found for $TeO_2$ at any concentration that was tested.

EXAMPLE 15

Using the procedure of Example 4, human mononuclear cells were tested for their ability to produce IL-2 after induction with PHA or in unstimulated cells from normal donors and from patients suffering from systemic lupus erthyrematous. The IL-2 content was tested according to the procedure of Example 3 using the CTLD IL-2 dependent cell line. The results are reported in Table 5.

TABLE 5

| | | IL-2 PRODUCTION BY COMPLEX OF EXAMPLE I | | |
|---|---|---|---|---|
| SUBJECTS | PHA | 5 μg 0.2 mlPBS | 1:50PBS* | 1:100PBS* | 1:200PBS* |
| NORMAL | | | | | |
| 1 | − | 2.3** | 43.6 | 38.4 | 30.1 |
|   | + | 36.4 | 48.2 | 46.2 | 38.6 |
| 2 | − | 2.1 | 52.2 | 50.3 | 47.1 |
|   | + | 30.4 | 38.9 | 54.2 | 49.8 |
| 3 | − | 2.1 | 50.8 | 46.1 | 31.3 |
|   | + | 38.9 | 53.5 | 44.8 | 38.3 |
| SLE | | | | | |
| 1 | − | 2.0 | 37.3 | 32.1 | 26.1 |
|   | + | 6.3 | 24.2 | 19.7 | 15.4 |
| 2 | − | 2.4 | 43.6 | 35.1 | 30.3 |
|   | + | 8.2 | 28.1 | 24.0 | 18.6 |
| 3 | − | 2.4 | 19.2 | 18.1 | 14.4 |
|   | + | 4.1 | 23.8 | 20.2 | 16.8 |

*Dilution of 1 part of 0.2 ml of PBS containing 5 μg of complex of Ex 1 in 50, 100 or 200 parts of PBS.
**CPM × $10^{-3}$ of. $^3$H Thymidine of $5 \times 10^{-4}$ CTLD cells in presence of 1:2 dilution of the supernatants as in Ex. 3.

EXAMPLE 16

This example provides an assay to detect the presence of receptor sites for IL-2. Human mononuclear cells were incubated for 24 hours in the presence of the complex of Example 1 and $TeO_2$. The cells were washed twice with PBS and then incubated with a specific fluoresceinated antibody against IL-2 receptors as described in Uchiyama et al, J. Immunol. 126, 1398 (1981) The results were that in the control 2% of the cells were positive; in the presence of PHA 80% of the cells were positive and with 1 μg/ml of the complex of Example 1, 20% of the cells were found to be positive. It was found that $TeO_2$ gave 5% positive cells at a level of 1 μg/ml.

EXAMPLE 17

The effect of the complex of Example 1 on an infection with West Nile virus (WNV) was determined. WNV is a toga virus of the flavivirus group, a positive single stranded RNA virus, which when injected IP to mice usually kills them within 5-8 days as a result of extensive damage to the central nervous system. For this study ICR mice (3 wks of age) were Injected IP with the virus at the concentration of $10^3$ or $10^4$ $LD_{50}$ units/mouse. Injections of 10 μg/0.2 ml PBS/mouse of the complex of Ex. 1 were given on day −1 (one day prior to injection of virus) and 6 days after injection of virus. Table A shows preliminary results of one such experiment. As can be seen, after 8 days all animals injected with the virus alone died, whereas three out of five animals receiving treatment with the complex of Ex. 1 remained alive.

TABLE A

| Treatment | $10^3 LD_{50}$ | $10^3 LD_{50}$ | $10^4 LD_{50}$ | $10^4 LD_{50}$ | 0 |
|---|---|---|---|---|---|
| Complex injected | NO | YES | NO | YES | YES |
| # Alive/Total | 0/6 | 3/5 | 0/6 | 3/5 | 6/6 |

In a second experiment, mice were injected with $10^3$ $IPLD_{50}$ virus and received injections of the complex of Example 1 (10 μg/0.2 ml PBS/mouse) on days −1, 1, 2 and 4. Preliminary results of one such experiment on day 8 after injection are shown in Table B. As seen on day 8 all animals injected with virus alone died whereas 3 out of 5 receiving the complex of Ex. 1 remained alive. Two out of the remaining three survived an additional 8 days, whereas the third remained alive without any manifestations of clinical symptoms.

TABLE B

| Treatment | $10^3 IPLD_{50}$ | ($10^3 IPLD_{50}$ + Complex) | Complex |
|---|---|---|---|
| # Alive/Total | 0/8 | 3/5 | 5/5 |

EXAMPLE 18

This example shows that the interaction of WNV with cultures of ICR mouse macrophage results in a productive infection. Varying amounts of the complex of Example 1 (5 μg, 1 μg, 0.1 μg) were incubated with a monolayer of mouse macrophages for 24 h. After 24 h macrophages incubated with 5 μg of the complex of Example 1 died whereas others remained unaffected. All cultures were then infected with $10^4$ PFU/plate. After 72 h incubation the supernatants were collected and the virus was titrated against Vera cells. Table A shows preliminary results of one such experiment. As can be seen, incubation of macrophage cultures with 1 μg of the complex of Example 1 resulted in a 40-fold reduction of virus yield, whereas incubation with 0.1 μg of the complex of Ex. 1 plate resulted in a ten-fold reduction in virus yield.

TABLE A

| Treatment | Virus Yield (PFU/ml) |
|---|---|
| Control (virus alone) | $2 \times 10^4$/ml |
| Complex of Example 1 μg/plate | $5 \times 10^2$/ml |
| Complex of Example 1 0.1 μg/plate | $2 \times 10^3$/ml |

EXAMPLE 19

To test the efficacy of the complex of Example 1 as a potential cancer therapy agent, independent of its cytokine-increasing effect in the animal body, the inhibition of growth of Ha-Ras transformed NIH-3T3 cells was assessed.

Method:

$5 \times 10^2$ cells were plated per 60 mm dish and incubated with different concentrations (0.005-5 µg/ml) of the complex in PBS. A week later, the cells were stained with Gimsa and clones were counted. Similar experiments were conducted using V-mos transformed NIH-3T3 cells, and also using $Ph_2TeCl_2$ and $Ph_3TeCl$, with both types of transformed cells.

Results:

(a) there was a major reduction in the number of colonies of Ha-Ras transformed NIH-3T3 cells treated with the present complex, compared with control, whereas $Ph_2TeCl_2$ and $Ph_3TeCl$ did not inhibit their growth;

(b) none of the complex, $Ph_2TeCl_2$ or $Ph_3TeCl$ inhibited the growth of V-mos transformed NIH-3T3 cells, (c) there was a consistent correlation between the extent of inhibition of Ha-Ras transformed NIH-3T3 cells treated with the present complex, and the concentration of complex used, the maximum effect being attained with a concentration of 0.05 µg/ml.

CONCLUSIONS

The tested complex inhibits growth of Ha-Ras transformed NIH-3T3 cells independently of its cytokine increasing characteristics, and is thus a potential cancer therapy agent. The lack of similar biological activity by $Ph_2TeCl_2$ or $Ph_3TeCl$ is presumably due to the fact that these compounds, in aqueous media, are structurally incapable of giving rise to the present complexes. Additionally, the fact that the complex did not inhibit the growth of V-mos transformed NIH-3T3 cells, suggests that the antiproliferative effect of the complex may be mediated via p21 Ras protein.

While particular embodiments of the invention have been particularly described hereinabove, it will be appreciated that the present invention is not limited thereto, since as will be readily apparent to skilled persons, many modifications or variations can be made. Such modifications or variations which have not been detailed herein are deemed to be obvious equivalents of the present invention.

The invention claimed is:

1. A method for stimulating cells to produce cytokines, which comprises contacting cytokine producing cells with an aqueous solution comprising at least one species selected from the group consisting of a 1:1 molar non-covalent complex of $TeO_2$ with a moiety of formula (A) and ammonium salts thereof:

    HO—X—OH    (A)

where X is an optionally substituted divalent saturated hydrocarbon group containing 2-8 carbon atoms in the chain connecting the two OH groups.

2. A method according to claim 1, wherein lymphokine producing cells are contacted in vivo.

3. A method according to claim 1, wherein lymphokine producing cells are contacted in vitro.

4. A method for treatment of a mammalian disease or condition responsive to increased production of cytokines and(or) their receptors in the mammalian body and which is selected from cancer, immune deficiencies, autoimmune diseases, neurodegenerative diseases and infectious diseases, wherein a mammal having said disease or condition is treated with a medicament including an aqueous solution comprising at least one species selected from the group consisting of a 1:1 molar non-covalent complex of $TeO_2$ with a moiety of formula (A) and ammonium salts thereof:

    HO—X—OH    (A)

where X is an optionally substituted divalent saturated hydrocarbon group containing 2-8 carbon atoms in the chain connecting the two OH groups, and the amount of complex of formula (A) present in said medicament is an amount which is effective for said treatment.

5. A method for treatment of a mammalian cancer which is essentially unresponsive to increased production of cytokines and(or) their receptors in the mammalian body, wherein a mammal having said cancer is treated with a medicament including an aqueous solution comprising at least one species selected from the group consisting of a 1:1 molar non-covalent complex of $TeO_2$ with a moiety of formula (A) and ammonium salts thereof:

    HO—X—OH    (A)

where X is an optionally substituted divalent saturated hydrocarbon group containing 2-8 carbon atoms in the chain connecting the two OH groups, and the amount of complex of formula (A) present in said medicament is an amount which is effective for said treatment.

6. A method for stimulating cells to produce cytokines, which comprises contacting cytokine producing cells with a pharmaceutical composition which comprise at least one pharmaceutical carrier, diluent or adjuvant, and an aqueous solution comprising at least one species selected from the group consisting of a 1:1 molar non-covalent complex of $TeO_2$ with a moiety of formula (A) and ammonium salts thereof:

    HO—X—OH    (A)

where X is an optionally substituted divalent saturated hydrocarbon group containing 2-8 carbon atoms in the chain connecting the two OH groups.

7. A method according to claim 6, wherein lymphokine producing cells are contacted in vivo.

8. A method according to claim 6, wherein lymphokine producing cells are contacted in vitro.

* * * * *